(12) United States Patent
Shlomchik et al.

(10) Patent No.: US 7,288,255 B1
(45) Date of Patent: Oct. 30, 2007

(54) PREVENTION OF IMMUNOREACTIVITY BY DEPLETING OR INHIBITING ANTIGEN PRESENTING CELLS

(75) Inventors: Warren D. Shlomchik, Stratford, CT (US); Mark Jay Shlomchik, Woodbridge, CT (US); Stephen G. Emerson, Wayne, PA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/568,834

(22) Filed: May 11, 2000

Related U.S. Application Data

(63) Continuation of application No. PCT/US98/24183, filed on Nov. 12, 1998.

(60) Provisional application No. 60/065,198, filed on Nov. 12, 1997.

(51) Int. Cl.
| | |
|---|---|
| A61K 39/395 | (2006.01) |
| A01N 63/00 | (2006.01) |
| C07K 16/00 | (2006.01) |
| C07K 17/00 | (2006.01) |
| C12P 21/08 | (2006.01) |

(52) U.S. Cl. ............... 424/183.1; 424/178.1; 424/93.7; 530/387.1; 530/387.3; 530/388.7; 530/391.7

(58) Field of Classification Search ............. 435/320.1, 435/325; 530/350, 387.1, 387.3, 388.7, 391.7; 424/93.2, 93.21, 170.1, 93.7, 183.1; 514/44
See application file for complete search history.

(56) References Cited

U.S. PATENT DOCUMENTS
5,239,062 A    8/1993  Blattler et al.

FOREIGN PATENT DOCUMENTS
WO    WO93/04187    3/1993

OTHER PUBLICATIONS

Deonarain; Ligand-targeted receptor-mediated vectors for gene delivery, 1998, Exp. Opin. Ther. Patents 8: 53-69.*
Miller et al.; Targeted v ectors for gene therapy, 1995, FASEB J 9: 190-199.*
Reiter et. al., Peptide-specific killing of antigen-presenting cells by a with T cell receptor-like specificity, 1997. Proc Natl Acad. Sci., vol. 94: 4631-4636.*
Deonarain. Ligand-targeted receptor-mediated vectors for gene delivery. 1998. Exp. Opin. Ther. Patents. 8, 53-69.*
Miller et al. Targeted vectors for gene therapy. 1995. FASEB J. 9, 190-199.*
Francisco et al. In vivo efficacy and toxicity of a single-chain immunotoxin targeted to CD40. 1997. Blood, 89 (12), 4493-4500.*
Hu et al. Depletion of T lymphocytes with immunotoxin retards the progress of experimenatal allergic encephalomyelitis in rhesus monkeys. 1997. Cellular Immunology. 177, 26-34.*
Sekine, et al., Oct. 1997, Role of Passenger Leukocytes in Allograft Rejection, J. Immunol., vol. 159, pp. 4084-4093.
Arnold, et al., 1995, J. Exp. Med., 182:885-889.
Arnold, et al., 1997, J. Exp. Med. 186:461-466.
Banchereau, et al., 1998, Nature 392:245-252.
Basclga, et al., 1998, Cancer Res., 58:2825-2831.
Bera, et al., 1998 Molecular Medicine, 4:384-391.
Bevan, 1976, J. Exp. Med., 143:1283-1 288.
Bevan, 1995, J. Exp. Med. 182:639-641.
Bird, et al., 1988, Science, 242:423-426.
Bix, et al., 1991, Nature, 349:329-331.
Bolognesi, et al., 1998 Brit. J. Haematoli, 101:179-188.
Bonini, et al., 1997, Science, 276:1719-1 724.
Bordignon, et al., 1995, Human Gene Therapy, 6:813-819.
Braun, et al., 1990, Biology of Reproduction, 43:684-693.
Burbage, et al., 1997, Leukemia Res., 21:681-690.
Burton, et al., 1994, Adv. Immunol., 57:191-280.
Carbone, et al., 1989, Cold Spring Harbor Symp. Quant. Biol., 1:551-555.
Carbone, et al., 1990, J. Exp. Med., 171:377-387.
Champlin, 1993, Leukemia and Lymphoma, 11:149-152.
Chandler, et al., 1996, Seminars in Pediatric Surgery, 5:206-211.
Collins, et al., 1994, Blood, 84:333a.
Collinson, et al., 1994, J. Immunopharmacology, 16:37-49 (p. 42 intentionally omitted).
Conry, et al., 1995, J. Immunotherapy, 18:231-241.
Essand, et al., 1998, Internatl. J. Cancer, 77:123-127.
Faguet, et al., 1997, Leukemia & Lymphoma, 25:509-520.
Ferrara, 1993, Curr. Opinion in Immunol., 5:794-799.
Ferrara, et al., 1993, Transplantation Proceedings, 25:1216-1217.
Ferrara, et al., 1994, Bone Marrow Transplantation, 14:183-184.
Flavell, et al., 1995, Brit. J. Cancer, 72:1373-1379.
Francisco, et al., 1998, Leukemia and Lymphoma, 30:237-245.
Frankel, et al., 1997, Leukemia & Lymphoma, 26:287-298.
Gaziev, et al., 1997, Transplantation, 63:854-860.
Germain, 1994, Cell, 76:287-299.
Ghetie, et al., 1997, Mol. Med. 3:420-427.
Gu, et al., 1997, Thrombosis and Hematocyst, 77:755-759.
Horowitz, et al., 1990, Blood 75:555-562.
Huston et al., 1988, Proc. Natl. Acad. Sci. USA, 85:5879-5883.
Huang et al., 1996, Immunity, 4:349-355.
Huang, et al., 1994, Science, 264:961-965.
Koller, et al., 1990, Science 248:1227-1230.
Knowles, et al., 1987, Anal. Biochem., 160:440-443.
Kolb, et al., 1995, Blood, 86:2041-2050.
Korngold, et al., 1982, J. Exp. Med. 155:872-883.
Korngold, et al., 1983, Immunol. Rev., 71:5-29.
Korngold, et al., 1987, Transplantation, 44:335-339.
Korngold, et al., 1987, J. Exp. Med., 165:1552-1564.
Kreitman, et al., 1997, Blood, 90:252-259.
Kreitman, et al., 1998, Advanced Drug Delivery Reviews, 31:53-88.
Kurts, et al., 1998, J. Exp. Med., 188:409-414.

(Continued)

*Primary Examiner*—Anne Marie Wehbé
(74) *Attorney, Agent, or Firm*—Cooley Godward LLP

(57) ABSTRACT

The invention includes compositions and methods for depleting antigen presenting cells, or for impairing the biological function of antigen presenting cells, which compositions are useful for treatment of graft versus host disease and other immune diseases.

9 Claims, 9 Drawing Sheets

OTHER PUBLICATIONS

Kuzel, et al., 1993, Leukemia & Lymphoma, 11:369-377.
Lammert, et al., 1997, Eur. J. Immunol., 27:923-927.
LeMaistre, et al., 1993, Cancer Res., 53:3930-3934.
Levy, et al., 1991, J. Clin. Oncol., 9:537-538.
Lucarelli, et al., 1997, Cancer Treatment and Research, 77:305-315.
Lynch, et al., 1997, J. Clin. Oncol., 15:723-734.
Mackall, et al., 1993, Blood, 82:2585-2594.
Mackall, et al., 1997, Blood, 89:3700-3707.
Mackall, et al., 1997, Immunol. Today, 18:245-251.
Mansfield, et al., 1997, Blood, 90:2020-2026.
Maraskovsky, et al., 1996, J. Exp. Med., 184:1953-1962.
Marks, et al., 1991, J. Mol. Biol., 222:581-597.
Matzinger, 1977, Cell. Immunol. 33:92-100.
Maurer-Gebhard, et al., 1998, Cancer Res., 58:2661-2666.
Metlay, et al., 1990, J. Exp. Med., 171:1753-1771.
Minasi, et al., 1993, J. Exp. Med., 177:1451-1459.
Moreland, et al., 1995, Arthritis & Rheumatism, 38:1177-1186.
Nielsen, et al., 1991, Science, 254:1497-1500.
O'Marcaigh, et al., 1997, Curr. Opinion in Oncol. 9:126-130.
O'Toole, et al., 1998, Curr. Topics In Microbiol. & Immunol. 234:35-56.
Press, et al., 1998, Cancer Journal from Scientific American, 4:S19-S26.
Przepiorka, et al., 1995, Bone Marrow Transplantation, 16:737-741
Rowe, et al., 1994, Anal. Int. Med. 120:143-158.
Schnell, et al., 1996, Internatl. J. Cancer, 66:526-531.
sprent, et al., 1998, J. Exp. Med., 167:556-569.
Spyridonidis, et al., 1998, Blood, 91:1820-1827.
Srivastava et al., 1994, Immunogenetics, 39:93-98
Sullivan, et al., 1986, Blood, 67:1172-1175.
Sullivan, et al., 1989, New Engl. J. Med., 320:828-834
Truitt, et al., 1991, Blood, 77:2515-2523.
Tuszynski, et al., 1988, Blood, 72:109-115.
Udono, et al., 1993, J. Exp. Med., 178:1391-1396.
Winkler, et al., 1997, Annals of Oncol., 8:139-146.
Wright, et al., 1992, Critical Rev. in Immunol., 12:125-168.
Wu, 1997, Brit J. Cancer, 75:1347-1355.
Zdanovsky, et al., 1997, Faseb Journal, 11:A1325-A1325.
Anderson et al. (2005) "Distinct roles for donor-and host-derived antigen-presenting cells and costimulatory molecules in murine chronic graft-versus-host disease: requirements depend on target organ" Blood 105: 2227-2234.

Bertolini et al. (1997) "A new "two step" procedure for 4.5 log depletion of T and B cells in allogeneic transplantation and of neoplastic cells in autologous transplantation" Bone Marrow Transplant 19: 615-619.
Clark et al. (1994) "Antigen-specific deletion of cloned T cells using peptide-toxin conjugate complexed with purified class II major histocompatibility complex antigen" J. Biol. Chem. 269: 94-99.
Francisco et al. (1997) "Construction, Expression, and Characterization of BD1-G28-5 sFv, a Single-chain Anti-CD40 Immunotoxin Containing the Ribosome-inactivating Protein Bryodin 1" J. Biol. Chem. 272(39): 24165-24169.
Freeman et al. (1997) "Immune system in suicide-gene therapy" The Lancet 349: 2-3.
Kreitman et al. (1998) "Immunotoxins for targeted cancer therapy" Adv. Drug Deliv. Rev. 31:53-88.
Matte et al. (2004) "Donor APCs are required for maximal GVHD but not for GVL" Nature Medicine 10: 987-992.
Mullen et al. (1994) "Metabolic suicide genes in gene therapy" Pharmacol. Ther. 63(2): 199-207.
Reff et al. "Depletion of B cells in vivo by a chimeric mouse human monoclonal antibody to CD20" Blood 83(2): 435-445.
Rooijen et al. (1992) "Efficacy of various water-soluble chelator molecules in the liposome-mediated macrophage"suicide" technique" Journal of Pharmacological and Toxicological Methods, 28: 217-221.
Schultz et al. (1995) "Requirement for B cells in T cell priming to minor histocompatibility antigens and development of graft-versus-host disease" Bone Marrow Transplant 16: 289-295.
Shlomchik et al. (1997) "Radioresistant host antigen presenting cells are required for acute graft-versus host disease induction" Blood 90:396a.
Wong et al. (1984) "Depletion of macrophages from heterogeneous cell populations by the use of carbonyl iron" Methods in Enzymology 108: 307-313.
Slaper-Cortenbach, et al, "Effective Purging of Bone Marrow by a Combination of Immunorosette Depletion and Complement Lysis" Experimental Hematology, 18, No. 1, pp. 49-54 (Jan. 1990).
Uckun et al, "Developmental hierarchy during early human B-cell ontogeny after autologous bone marrow transplantation using autografts depleted of CD19+ B-cell precursors by an anti-CD19 pan-B-cell immunotoxin containing pokeweed antiviral protein" Blood 79, No. 12, pp. 3369-3379 (Jun. 15, 1992).

* cited by examiner

 
FIGURE 2A

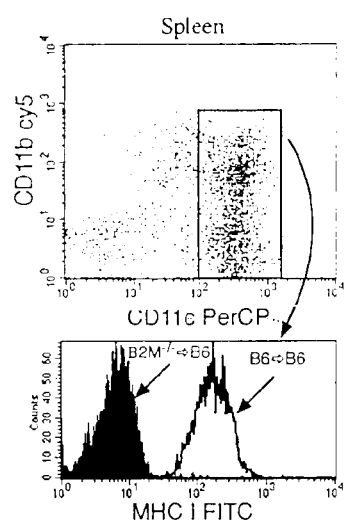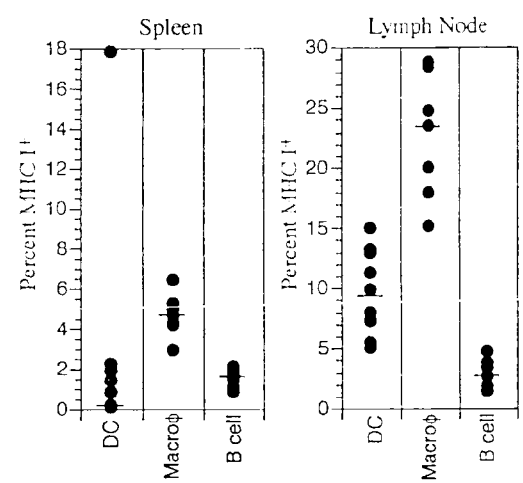
FIGURE 4A                    FIGURE 4B

| Group | N | Liver | | | Intestine | | | Tongue | | | Ear | | | Skin | | |
|---|---|---|---|---|---|---|---|---|---|---|---|---|---|---|---|---|
| | | + | +/- | - | + | +/- | - | + | +/- | - | + | +/- | - | + | +/- | - |
| B6⇒B6 BM/CD8 | 6 | 4 | 2 | 0 | 4 | 1 | 1 | 6 | 0 | 0 | 6 | 0 | 0 | 5 | 0 | 1 |
| $\beta_2M^{-/-}$⇒B6 BM/CD8 | 6 | 0 | 1 | 5 | 0 | 0 | 6 | 0 | 1 | 5 | 1 | 1 | 4 | 0 | 0 | 6 |
| B6⇒B6 BM | 3 | 0 | 2 | 1 | 0 | 2 | 1 | 0 | 0 | 3 | 0 | 0 | 3 | 0 | 0 | 3 |
| $\beta_2M^{-/-}$⇒B6 BM | 3 | 0 | 0 | 3 | 0 | 0 | 3 | 0 | 1 | 2 | 0 | 0 | 3 | 0 | 0 | 3 |

FIGURE 5

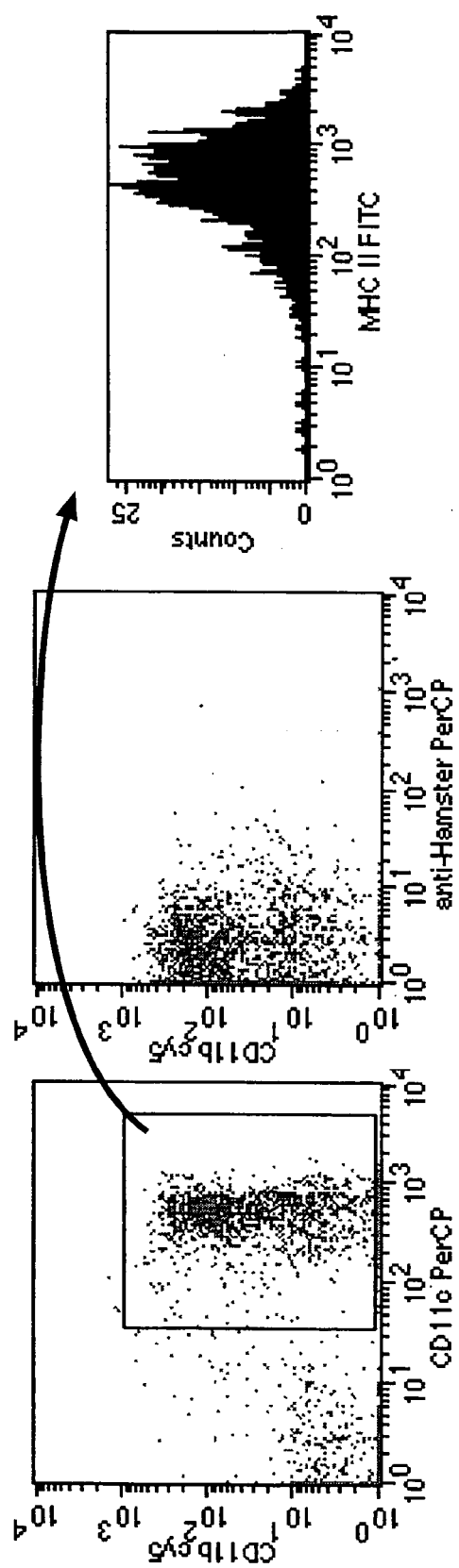

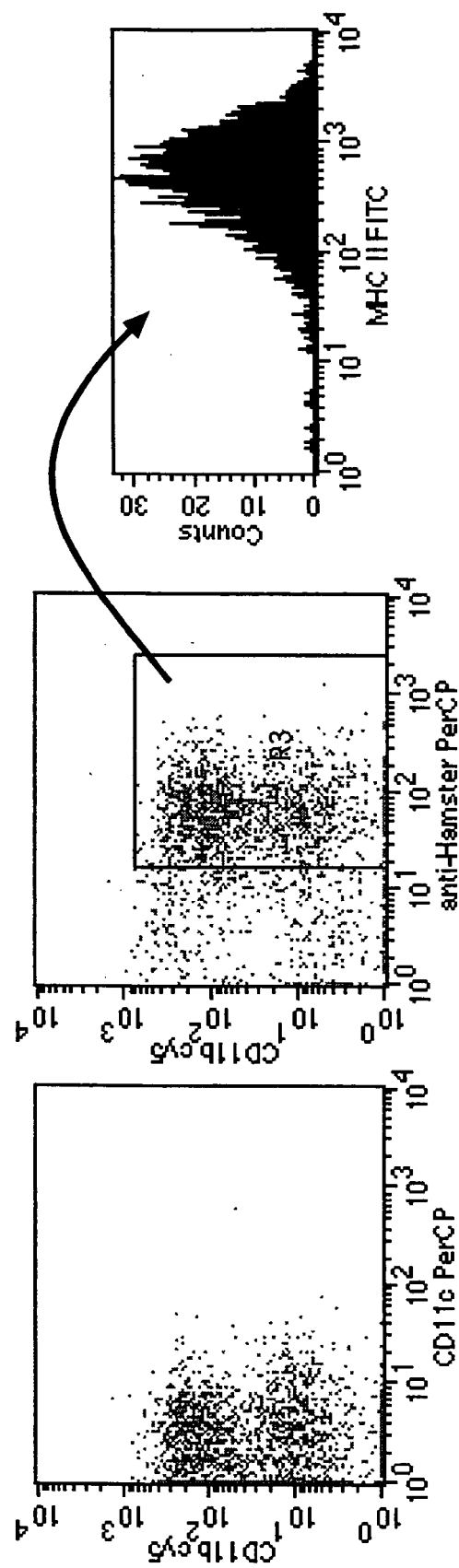

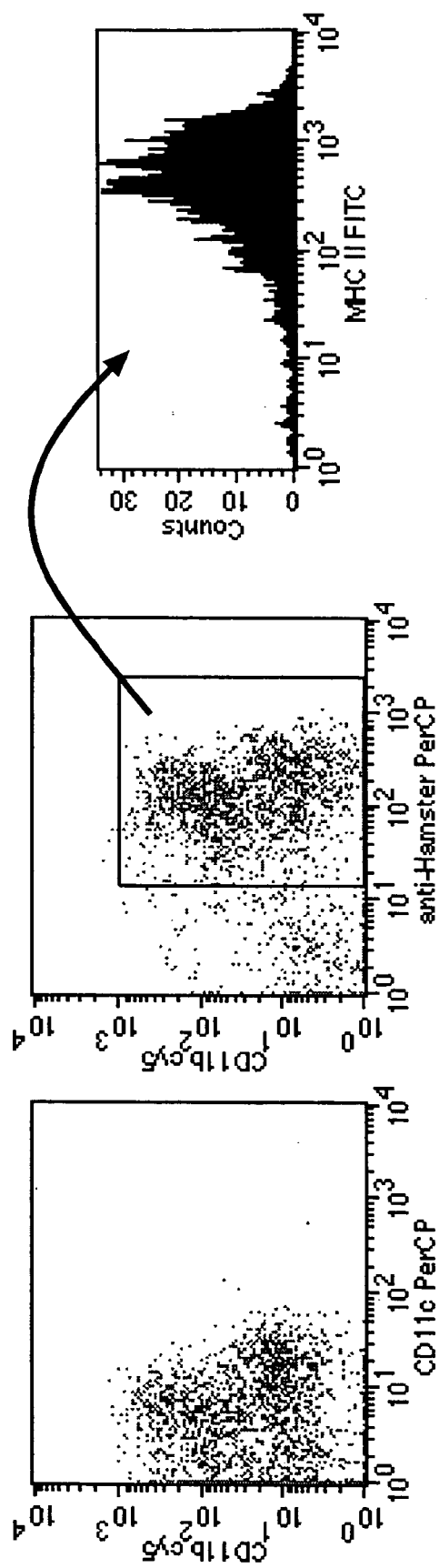

PREVENTION OF IMMUNOREACTIVITY BY DEPLETING OR INHIBITING ANTIGEN PRESENTING CELLS

This application is a continuation of International Application PCT/US98/24183, filed on Nov. 12, 1998, which claims priority to U.S. provisional application 60/065,198, filed on Nov. 12, 1997.

FIELD OF THE INVENTION

The field of the invention is depletion of antigen presenting cells.

BACKGROUND OF THE INVENTION

Allogeneic bone marrow transplantation (alloBMT) has revolutionized the treatment of chronic myelogenous leukemia, the acute leukemias, and aplastic anemia (Champlin, 1993, Leukemia and Lymphoma 2:149–152; Rowe et al., 1994, Anal. Int. Med. 120:143–158). In alloBMT, a patient receives intensive myeloablative chemotherapy and/or radiotherapy followed by the infusion of bone marrow (BM) from a donor, usually a major histocompatibility complex (MHC) matched sibling or increasingly an MHC matched unrelated donor. Unfortunately, Graft-versus-Host Disease (GVHD), an alloimmune attack against host tissues, remains a morbid toxicity that greatly limits the applicability and efficacy of alloBMT in treatment of both malignant and inherited diseases (Ferrara et al., Eds., 1996, Graft vs. Host Disease, Marcel Dekker, Inc., NY). In GVHD, T cells react against a subset of host peptides bound to MHC molecules, called minor histocompatibility antigens, which are derived from expression of polymorphic genes that distinguish the host from donor. Severe GVHD is associated with a nearly four-fold risk of treatment failure in alloBMT for early leukemia and remains the major barrier preventing an expanded use of alloBMT in treatment of genetic diseases such as sickle cell anemia and thalassemia major (Horowitz et al., 1990, Blood 75:555–562; O'Marcaigh et al., 1997, Curr. Opinion in Oncol. 9:126–130; Lucarelli et al., 1997, Cancer treatment and Research 77:305–315; Gaziev et al., 1997, Transplantation 63:854–860). Efforts to understand the nature of GVHD effector cells and inflammatory cytokines released during GVHD reactions have not yet translated into approaches for managing clinical GVHD beyond immunosuppression directed largely against T cells.

Most T cell responses are initiated on so called "professional" antigen presenting cells (APCs). However, the roles of host and donor derived APCs in initiating GVHD have not been thoroughly examined. Further, targets for more specific GVHD therapy are at present unknown. The mechanism of antigen presentation to GVHD effector cells has been little studied and is not clearly understood (Korngold et al., 1983, Immunol. Rev. 71 5–29; Korngold et al., 1982, J. Exp. Med. 155:872–883). Antigen presentation in alloBMT is unique in that from the time the donor marrow cells are infused, both host and donor APCs could potentially stimulate T cells mediating GVHD. Since the BM of recipients is ablated by cytotoxic therapies prior to the transplant, one might assume that recipient APCs would not be available to initiate GVHD. Consistent with this reasoning, increasing the intensity of the ablative protocol does not reduce GVHD, but instead increases its severity (Truitt et al., 1991, Blood 77:2515–2523). On the other hand, since MHC Class I (MHC I) restricted CD8$^+$ T cells play a central role in GVHD, one might suspect that recipient APCs would be required (Sprent et al., 1988, J. Exp. Med. 167:556–569; Korngold et al., 1987, Transplantation 44:335–339; Korngold et al., 1987, J. Exp. Med. 165:1552–1564). This is because on a given cell the peptide antigens presented by its MHC I molecules to CD8 T cells are derived largely from expression of genes within that cell. Donor derived APCs would therefore not have ready access to such host peptides as they do not express the host polymorphic genes that encode GVHD target antigens (Germain, 1994, Cell 76:287–299). However, recent data has demonstrated that extracellular antigens can be introduced into the MHC I antigen presentation pathway, a phenomenon dubbed "cross priming" (Matzinger et al., 1977, Cell. Immunol. 33:92–100; Bevan, 1976, J. Exp. Med. 143:1283–1288; Bevan, 1995, J. Exp. Med. 182:639–641; Carbone et al., 1989, Cold Spring Harbor Symp. Quant. Biol. 1:551–555; Huang et al., 1994, Science 264:961–965; Huang et al., 1996, Immunity 4:349–355; Srivastava et al., 1994, Immunogenetics 39:93–98; Arnold et al., 1995, J. Exp. Med. 182:885–889)

Experiments to date have not yet determined which source(s) of APCs, donor or host, are required for GVHD initiation. The resolution of this issue is of great practical as well as theoretical importance. Understanding the roles of donor and host APCs in GVHD induction will direct distinct and novel strategies for reducing GVHD by specifically targeting either population.

There is a long felt need in the art for the development of specific mechanisms for reducing GVHD in animals, particularly in humans. The present invention satisfies this need.

SUMMARY OF THE INVENTION

The invention includes a method of depleting antigen presenting cells in a population of hematopoietic cells. The method comprises contacting the hematopoietic cells with an antigen presenting cell depleting composition to effect impairment of antigen presenting cell function or killing of the antigen presenting cells, thereby depleting the antigen presenting cells in the population of hematopoietic cells.

In one aspect, the antigen presenting cells are selected from the group consisting of dendritic cells, B lymphocytes and macrophages.

In another aspect, the depleting is performed in vitro.

In yet another aspect, the depleting is performed in vivo in a mammal.

In a preferred embodiment, the hematopoietic cells are human hematopoietic cells.

In another aspect, the antigen depleting composition is selected from the group consisting of a toxin, an antibody, a radioactive molecule, a nucleic acid, a peptide, a peptidomemetic and a ribozyme.

In a preferred embodiment, the toxin is an immunotoxin. More preferably, the toxin is selected from the group consisting of ricin, diptheria toxin and pseudomonas exotoxin A.

In another preferred embodiment, the antibody is selected from the group consisting of antibody specific for CD1a, antibody specific for CD11c, antibody specific for MHCII, antibody specific for CD11b, antibody specific for DEC205, antibody specific for B71, antibody specific for B72, antibody specific for CD40, antibody specific for Type I lectins and antibody specific for Type II lectins.

In yet another preferred embodiment, the nucleic acid molecule is selected from the group consisting of a gene and an oligonucleotide.

In a further preferred embodiment, the radioactive molecule is a radioactively labeled antibody.

In another preferred embodiment, the antigen depleting composition is a chimeric composition comprising an antibody and a toxin. Preferably, the toxin is selected from the group consisting of ricin, diptheria toxin and pseudomonas exotoxin A.

In another preferred embodiment, the antibody is selected from the group consisting of antibody specific for CD1a, antibody specific for CD11c, antibody specific for MHCII, antibody specific for CD11b, antibody specific for DEC205, antibody specific for B71, antibody specific for B72, antibody specific for CD40, antibody specific for Type I lectins and antibody specific for Type II lectins.

In yet another aspect of the invention, the antigen depleting composition is delivered to the antigen presenting cell in a vector selected from the group consisting of a viral vector and a non-viral vector.

Also include in the invention is a method of preventing graft versus host disease in a mammal. The method comprises contacting a population of hematopoietic cells in the mammal with an antigen presenting cell depleting composition to effect depletion of antigen presenting cells in the population of hematopoietic cells, and transferring donor hematopoietic cells to the mammal, wherein the graft versus host disease is prevented in the mammal by virtue of the depletion of the antigen presenting cells.

In one aspect, the mammal is a human.

In another aspect, the antigen presenting cell depleting composition is selected from the group consisting of a toxin, an antibody, a radioactive molecule, a nucleic acid, a peptide, a peptidomemetic and a ribozyme.

In yet another aspect, the antigen presenting cells are selected from the group consisting of dendritic cells, B lymphocytes and macrophages.

In a further aspect, the antigen presenting cell depleting composition is an antibody.

The invention also includes an antigen presenting cell depleting composition suspended in a pharmaceutically acceptable carrier.

Further included in the invention is a method of preventing graft versus host disease in a mammal. The method comprises obtaining a population of hematopoietic stem cells from the mammal, adding to the cells a gene which when expressed in the cells is capable of killing the cells, selecting cells having the gene incorporated therein, irradiating the mammal to remove bone marrow cells in the mammal, adding the selected cells to the mammal, inducing expression of the gene in the selected cells in the mammal thereby effecting killing of antigen presenting cells in the mammal, providing the mammal with an allogenic bone marrow transplant, wherein graft versus host disease is prevented in the mammal by virtue of the killing of the antigen presenting cells.

In one embodiment, the gene is operably linked to an inducible promoter and expression of the gene is effected by administration of an inducer of the promoter to the mammal.

In another embodiment, the gene encodes a toxin.

Also included is a method of preventing graft versus host disease in a mammal. The method comprises obtaining a population of hematopoietic stem cells from the mammal, adding to the cells a gene which when expressed in the cells in the presence of a corresponding agent is capable of killing the cells, selecting cells having the gene incorporated therein, irradiating the mammal to remove bone marrow cells in the mammal, adding the selected cells to the mammal, adding the corresponding agent to the mammal to effect killing of the selected cells in the mammal thereby effecting killing of antigen presenting cells in the mammal, providing the mammal with an allogenic bone marrow transplant, wherein graft versus host disease is prevented in the mammal by virtue of the killing of the antigen presenting cells.

In one embodiment, the gene is thymidine kinase, the gene is operably linked to a constitutive promoter and the corresponding agent is ganciclovir.

In another embodiment, the gene is thymidine kinase, the gene is operably linked to an inducible promoter, the corresponding agent is ganciclovir, and prior to adding the corresponding agent to the mammal, the expression of the gene is induced by administration of an inducer of the promoter to the mammal.

BRIEF DESCRIPTION OF THE DRAWINGS

FIG. 2 is a series of images depicting the fact that B6⇒B6 CD8 recipients develop GVHD. FIG. 2A depicts clinical GVHD. Representative $\beta_2 M$-/-⇒B6 C3H.SW T$^-$BM and CD8 recipient (left) and B6⇒B6 C3H.SW T$^-$BM and CD8 recipient (right) from experiment 1 are shown.

FIG. 4 are two illustrations depicting MHC I expression on macrophages, dendritic cells and B lymphocytes. FIG. 4A depicts MHC I expression of dendritic cells (DC). Dendritic cells were isolated by first collagenase treating spleens and lymph nodes followed by centrifugation through 30% BSA. Dendritic cells were identified by 4 color flow cytometry. Cells staining with a multi lineage cocktail of antibodies against Thy1.2 (T cells), Gr-1 (granulocytes), TERR 119 (erythroid), and CD45R (B220; B cells) were first excluded. Then dendritic cells that were either CD11c⁺/CD11b$^{31}$ or CD11c⁺/CD11b⁺ were gated on separately, and MHC I expression was examined. FIG. 4B depicts MHC I expression on dendritic cell (DC), macrophage (macroφ), and B cells in lymph nodes and spleens of β$_2$M$^{-/-}$⇒B6 chimeras. ● individual mouse; – median. 12 and 11 mice were analyzed for splenic dendritic cell chimerism; 7 mice were analyzed for macroφ and B cell chimerism.

FIG. 5 is a Table depicting histologic scoring of GVHD. Formalin fixed, paraffin imbedded sections were stained with hematoxylin and eosin, randomized and read blindly. Findings were scored according to established criteria and were given an overall interpretation of positive (+), indefinite (+/-), or negative (-) for GVHD. N=number of mice analyzed.

FIG. 6 is a series of illustrations depicting the fact that in vivo α-CD11c treatment completely stains dendritic cells. Spleens obtained from mice treated with two intraperitoneal (i.p.) injections of phosphate buffered saline (PBS; panels A–D) or 500 μg of a hamster monoclonal antibody against CD11c (clone 33D 1; panels E and F) were dispersed and digested with collagenase. The light fraction enriched for dendritic cells was separated by centrifugation on 30% BSA. Dendritic cells were identified by flow cytometry. Cells staining with a multi lineage cocktail of phycoerythrin conjugated antibodies against CD3 (T cells), TERR 119 (erythroid cells), Gr-1 (granulocytes), and CD45R (B220; B cells) were first excluded. Then the remaining cells were assessed for expression of CD11b and CD11c (CD11b cy5 and biotin-CD11c with a strepavidin PerCP (SA-PerCP) second step reagent). In the PBS treated mice, CD11c+ dendritic cells were easily identified and expressed high levels of MHC II as expected (histograms to the right of dot plots). If the cells obtained from PBS treated mice were first incubated with purified 33D1, CD11c+ dendritic cells could no longer be identified using anti-CD11c (C). However, if these cells were detected using a biotin conjugated mouse α-hamster antibody followed by SA-PerCP instead of α-CD11c, they cells could again be visualized (D). Without 33D1 preincubation, staining with mouse anti-hamster antibody was negative (B). In mice treated with i.p. 33D1, direct staining with α-CD11c did not identify dendritic cells (E). However, staining with mouse α-hamster identified a population similar to that seen in A and D, suggesting that nearly all CD11c molecules on splenic dendritic cells were bound to 33D1 antibody and thus were unavailable for staining with labeled α-CD11c antibodies. Similar results were obtained using lymph node cells.

DETAILED DESCRIPTION OF THE INVENTION

Figure 1:
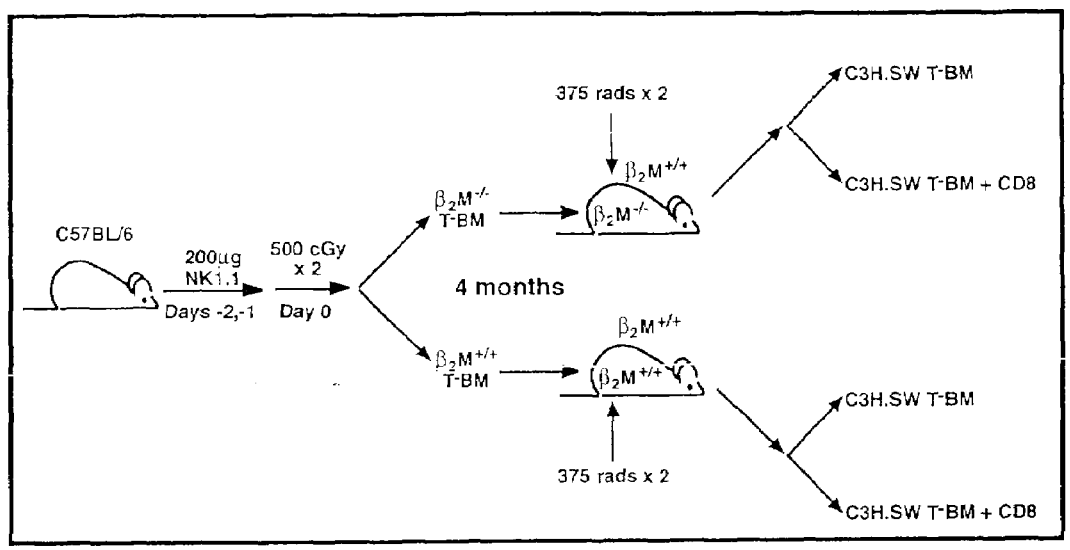
FIG. 1 is a diagram depicting the experimental protocol for the experiments presented in Example 1 herein. Eight to ten week C57BL/6 (H-$2^b$) mice received 200 μg of NK1.1 moAB intraperitoneally on days −2 and −1 to deplete natural killer cells and facilitate engraftment of B2M$^{-/-}$ cells (Bix et al., 1991, Nature 349:329–331). On day 0, mice received two 500 cGy fractions separated by 3 hours from a dual cesium radiator, followed by injection with $10^7$ T cell depleted bone marrow from C57BL/6 beta-2-microglobulin knock-out mice ($\beta_2 M^{-/-}$ T$^-$BM) or wild type C57BL/6 ($\beta_2 M^{+/+}$ T$^-$BM). Mice received acidified water and were kept in microisolator cages. Four months after the first transplant, chimeras were re-irradiated twice with 375 cGy fractions separated by 3 hours. Mice were then injected with 5–7×$10^6$ T cell depleted bone marrow cells obtained from C3H.SW (H-$2^b$) mice (C3H.SW T$^-$BM) with or without 1× or 2×$10^6$ purified C3H.SW CD8$^+$ T cells. Mice were examined for the development of GVHD.

Graft-vs.-Host Disease (GVHD), an alloimmune attack on host tissues mounted by donor T cells, is the most important toxicity of allogeneic bone marrow transplantation (alloBMT). The mechanism by which allogeneic T cells are initially stimulated has been unknown. The present invention is based on the development of a murine alloBMT model. In this model, in spite of the presence of numerous donor antigen presenting cells (APCs), only host-derived APCs initiated acute GVHD. This finding suggests a novel strategy for preventing GVHD, based on inactivating host APCs. This approach could greatly expand the safety and application of alloBMT in treatment of genetic and neoplastic diseases. In addition, this finding provides a basis for treating other diseases which have an autoimmune component, these diseases being discussed further elsewhere herein.

The data presented herein establishes that immune reactivity to normal tissues requires intact host APCs and that immune reactivity is preventable by depletion of host APCs.

Thus, the invention includes a method of depleting APCs in a host organism. Depletion of host APCs is beneficial to a host having a pathological immune response. In a preferred embodiment, host APCs are depleted prior to the administration to the host organism of donor hematopoietic cells, wherein the depletion of host APCs results in the absence of GVHD in the host organism upon receipt of the donor hematopoietic cells. Without wishing to be bound by theory, it is believed that it is the T cells in the donor population which are responsible for the graft versus host disease.

The preferred organism in which APCs are depleted is a human.

By the term "APC depleting composition" as used herein, is meant a composition which when contacted with an APC is capable of killing the APC or is capable of incapacitating the APC such that the APC is non-functional.

The terms "impairment of APC function" or "non-functional APC" are used essentially interchangeably herein and include an APC which is incapable of stimulating T cells in an antigen specific fashion. Thus, methods which impair APC function include any method which prevents an APC from stimulating T cells in an antigen specific fashion. Such methods include, but are not limited to, depleting APCs in a host and preventing APC costimulatory function. For example, antibodies, such as for example, antibodies directed against key costimulatory molecules such as B71 and/or B72 may be used to impair APC costimulatory function.

Depletion of APCs in an animal may be accomplished in any number of ways. For example, APC depletion may be accomplished using an immunotoxin conjugated to an antibody. The immunotoxin is a molecule which is capable of killing an APC, and may include, but not be limited to ricin, diptheria toxin, pseudomonas exotoxin A, ribosome inhibitory proteins, radioactivity, radiolabeled antibodies, or any other heretofore unknown or known toxin. Examples of suitable toxins and the methods of generating the same can be found in the following list of references. (Levy et al., 1991, J. Clin. Oncol. 9:537–538; Burbage et al., 1997, Leukemia Res. 21:681–690; Chandler et al., 1996, Seminars in Pediatric Surgery 5:206–211; Collinson et al., 1994, J. Immunopharmacology 16:37–49; Essand et al., 1998, Internatl. J. Cancer 77:123–127; Faguet et al., 1997, Leukemia & Lymphoma 25:509–520; Flavell et al., 1995, Brit. J. Cancer 72:1373–1379; Frankel et al., 1997, Leukemia & Lymphoma 26:287–298; Knowles et al., 1987, Anal. Biochem. 160:440–443; Kreitman et al., 1997, Blood 90:252–259; Lynch et al., 1997, J. Clin. Oncol. 15:723–734; Mansfield et al., 1997, Blood 90:2020–2026; Maurer-Gebhard et al., 1998, Cancer Res. 58:2661–2666; O'Toole et al., 1998, Curr. Topics in Microbiol. & Immunol. 234:35–56; Press et al., 1998, Cancer Journal From Scientific American 4:S19–S26; Przepiorka et al., 1995, Bone Marrow Transplantation 16:737–741; Schnell et al., 1996, Internatl. J. Cancer 66:526–531; Spyridonidis et al., 1998, Blood 91:1820–1827; Winkler et al., 1997, Annals of Oncol. 8:139–146; Kuzel et al., 1993, Leukemia & Lymphoma 11:369–377; Moreland et al., 1995, Arthritis & Rheumatism 38:1177–1186; LeMaistre et al., 1993, Cancer Res. 53:3930–3934).

Toxins may be generated using recombinant DNA methodology, or they may be obtained biochemically. When the toxin is obtained using recombinant DNA methodology, DNA encoding the toxin is cloned into a suitable vector, the vector is transfected into a suitable host cell and the toxin is generated in the host cell following transcription and translation of the DNA. Preferably, for the purposes of the present invention, DNA encoding the toxin is cloned in frame with DNA encoding a receptor or an antibody, which receptor or antibody is specific for a molecule expressed by an APC. Thus, the chimeric toxin molecule so generated is specific for an APC, targets the APC, binds thereto, and in some manner, effects impairment of or kills the APC.

Examples of toxins which are conjugated to an antibody or receptor molecule include the Pseudomonas A toxin. While the invention should in no way be construed to be limited to the use of this particular toxin, examples of chimeric molecules which include this toxin are provided in the following references to exemplify one embodiment of the invention. (Essand et al., 1998, Internatl. J. Cancer 77:123–127; Kreitman et al., 1997, Blood 90:252–259; Mansfield et al., 1997, Blood 90:2020–2026; Maurer-Gebhard et al., 1998, Cancer Res. 58:2661–2666; Spyridonidis et al., 1998, Blood 91:1820–1827; Bera et al., 1998, Molecular Medicine 4:384–391; Francisco et al., 1998, Leukemia & Lymphoma 30:237–245; Kreitman et al., 1998, Advanced Drug Delivery Reviews 31:53–88; Wu, 1997, Brit. J. Cancer 75:1347–1355; Zdanovsky et al., 1997, Faseb Journal 11:A1325–A1325).

By the term "immunotoxin" as used herein, is meant a compound which when in contact with an APC, is capable of killing the APC or incapacitating the APC such that the APC is non-functional.

In order to deplete APCs, the immunotoxin is preferably conjugated to an antibody, which antibody is specific for an epitope on an APC. Thus, the immunotoxin is directed to the APC by virtue of the antibody conjugated thereto. Epitopes which may be targeted on an APC include, but are not limited to, CD1a, CD11c, MHCII, CD11b, and DEC205. Additional epitopes include B71, B72, CD40, and Type I and Type II lectins. These are particularly attractive candidates as they can have cytoplasmic domains that signal for endocytosis when the receptor is engaged. Also included are matrix metalloproteins such as decysin, and chemokine receptors.

The antibody which is used may also be radioactively labeled, preferably, labeled with radioactive iodine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of protein molecules which form an immunoglobulin molecule. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988, Antibodies: A Laboratory Manual, Cold Spring Harbor, N.Y. Houston et al., 1988, Proc. Natl. Acad. Sci. USA 85:5879–5883; Bird et al., 1988, Science 242: 423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109–115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125–168) and the references cited therein. Further, the antibody of the invention may be "humanized" using the technology described in Wright et al., (supra) and in the references cited therein, and in Gu et al. (1997, Thrombosis and Hematocyst 77(4):755–759).

To generate a phage antibody library, a cDNA library is first obtained from mRNA which is isolated from cells, e.g., spleen cells or a hybridoma, which cells express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581–597. Panning of phage so generated for the isolation of a desired antibody is conducted in a manner similar to that described for phage libraries comprising Fab DNA.

APC depletion may also be accomplished by selectively introducing a gene into the APC, the expression of which gene either directly results in APC cell death or renders the APC specifically susceptible to other pharmacological agents. In vivo or ex vivo depletion of APCs according to this method may be accomplished by delivering the desired gene to the APC using a viral gene delivery systems such as, but not limited to a retrovirus, adenovirus or an adeno-associated virus gene delivery system. The desired viral delivery system may comprise a virus whose genome encodes a protein which, for example, directly causes cell death, for example by inducing apoptosis of the APC. Alternatively, the viral delivery system may contain a virus whose genome encodes, for example, a herpes simplex virus thymidine kinase gene. Expression of the herpes simplex virus thymidine kinase gene in the APC renders the APC sensitive to pharmacologic doses of ganciclovir. Thus, subsequent contact of the virally transduced APC with ganciclovir results in death of the APC. Such gene transfer approaches may be used in an ex vivo method of transducing human bone marrow, followed by infusion of bone marrow so transduced into the patient. These patients would then be treated with ganciclovir and then undergo a second therapeutic transplant of bone marrow in a manner similar to that described in the experimental examples presented herein.

Agents such as ganciclovir which mediate killing of a cell upon expression of a gene such as thymidine kinase, are referred to herein as "corresponding agents."

Hematopoietic stem cells can be collected from the patient by collecting aspirations from the iliac crest. This is performed under general anesthesia if large numbers are needed. More commonly, hematopoietic cells are obtained from the peripheral blood of the patient via leukopheresis. Leukopheresed patients may be pretreated with either chemotherapy or with hematopoietic growth factors such as GCSF and GMCSF in order to increase the numbers of circulating progenitor cells.

Genes which can be used to kill APCs include, but are not limited to, herpes simplex virus thymidine kinase and cytosine deaminase, or any gene which induces the death of a cell that can be placed under the control of an inducible promoter/regulatory sequence (referred to interchangeably herein as a "promoter/regulatory sequence" or as a "promoter"). The gene is transferred into a patient's primitive hematopoietic cells, the cells are selected under an appropriate selective pressure, the cells are transferred to the patient, and are allowed to engraft therein. The patient is then treated with an agent which induces promoter activity, thereby inducing expression of the gene whose product functions to kill APCs. In the case of thymidine kinase, other agents which facilitate killing of the cell by this enzyme may also be used, such as, for example, ganciclovir (Bonini et al., 1997, Science 276:1719–1724; Bordignon et al., 1995, Human Gene Therapy 6:813–819; Minasi et al., 1993, J. Exp. Med. 177:1451–1459; Braun et al., 1990, Biology of Reproduction 43:684–693). Other genes useful for this purpose include, but are not limited to, constitutively active forms of caspases 3, 8, and 9, bax, granzyme, diphtheria toxin, Pseudomonas A toxin, ricin and other toxin genes are disclosed elsewhere herein. The generation of appropriate constructs for delivery of such genes to a human will be readily apparent to the skilled artisan and is described, for example, in Sambrook et al. (1989, Molecular Cloning: A Laboratory Manual, Cold Spring Harbor Laboratory, New York) and in Ausubel et al. (1997, Current Protocols in Molecular Biology, John Wiley & Sons, New York).

It is important that the gene which is transferred into the cells, for the purpose of killing the cells, be placed under the control of the appropriate promoter sequence, such that induction of expression of the gene may be effected upon addition to the cells (administration to the mammal) of the appropriate inducer. Such inducible promoter sequences include, but are not limited to promoters which are induced upon addition of a metal to the cells, steriod inducible promoters and the like. In one preferred embodiment, the ecdysone promoter system may be employed. In this embodiment, the ecdysone promoter is cloned upstream of the ecdysone receptor protein sequence, which is positioned upstream of a second promoter sequence which drives expression of the ecdysone binding site operably linked to the desired gene, for example, the desired toxin. Induction of the promoter induces expression of the toxin, thereby effecting killing of the cell in which the toxin gene resides.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The use of viral and non-viral vectors for delivery of genes to hematapoietic cells is contemplated in the invention. Viral vectors include, but are not limited to, retroviral, adenoviral, herpesviral and other viral vectors which are well known in the art and are described, for example, in Sambrook et al. (1989, Molecular Cloning: A Laboratory Manual, Cold Spring Harbor Laboratory, New York) and in Ausubel et al. (1997, Current Protocols in Molecular Biology, John Wiley & Sons, New York). It is important of course, that any viral vector delivery system used employ a virus which is replication incompetent. As stated, non-viral vectors such as liposomes and the like, may also be used to deliver an APC depleting composition to a human.

Cells which have transduced therein a gene for cell killing, when such cells are transduced in an ex vivo manner, may be selected (i.e., separated from cells which do not comprise the gene) by providing the cells with a selectable marker in addition to the transduced gene. Selectable markers are well know in the art and are described, for example, in Sambrook et al. (1989, Molecular Cloning: A Laboratory Manual, Cold Spring Harbor, N.Y.).

APC depletion may further be accomplished by introducing into a population of APCs an oligonucleotide (for example, but not limited to, an antisense molecule) or a ribozyme, which oligonucleotide or ribozyme is capable of inducing death of the APC, or of inducing impairment of APC function. Such oligonucleotides include those which target an essential function of an APC, defined herein as being one which either kills an APC or impairs the function of the APC with respect to stimulation of T cells. Such functions of an APC include, but are not limited to, the costimulatory function of B71 and B72, CD40, among others. Thus, oligonucleotides and ribozymes which are useful in the methods of the invention include, but are not limited to, those which are directed against these targets.

Also included are oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used. The examples of oligonucleotide modifications described herein are not exhaustive and it is understood that the invention includes additional modifications of the antisense oligonucleotides of the invention which modifications serve to enhance the therapeutic properties of the antisense oligonucleotide without appreciable alteration of the basic sequence of the antisense oligonucleotide.

As used herein, the term "antisense oligonucleotide" means a nucleic acid polymer, at least a portion of which is complementary to a nucleic acid which is present in a normal cell. The antisense oligonucleotides of the invention preferably comprise between about fourteen and about fifty nucleotides. More preferably, the antisense oligonucleotides comprise between about twelve and about thirty nucleotides. Most preferably, the antisense oligonucleotides comprise between about sixteen and about twenty-one nucleotides.

As noted herein, depletion of APC includes impairment of APC function. Impairment of APC function includes all forms of APC impairment with or without physical removal or depletion of APCs. Thus, impairment of APC function includes the use of an antibody that blocks the function of APC surface molecules which are critical for APC function. Such APC surface molecules include, but are not limited to B71, B72 and DEC205. Antibodies directed against B71, B72 and CD40 are available from Pharmingen, San Diego, Calif. Anti-DEC205 antibodies and anti-MHC-II antibodies are available from Pharmingen and from the American Type Culture Collection.

Alternatively, peptides which block the function of APC surface molecules, which blocking results in impairment of APC function, may be used to effectively deplete APCs in a host organism. Such peptides include, but are not limited to, those which are designed to specifically bind receptor molecules on the surface of APCs, and those which are designed to, for example, inhibit essential enzymatic functions in these cells.

Similarly, genes and oligonucleotides which are designed for the same purpose as described herein, are also included as tools in the methods of the invention. Thus, peptides, oligonucleotides and genes which impair the biological function of an APC, as that term is defined herein, are also contemplated for use in the methods of the invention disclosed herein.

APC "depletion or impairment" as used herein, should be construed to include depletion of sufficient antigen presenting cells prior to or concurrent with allogenic bone marrow transplantation, including, but not limited to dendritic cells, B lymphocytes and macrophages to prevent graft versus host disease in the patient. The term should also be construed to include selective depletion of macrophages, selective depletion of dendritic cells, functional impairment of all antigen presenting cells including, but not limited to dendritic cells, macrophages, and B cells, selective functional impairment of macrophages, and selective functional impairment of dendritic cells.

The invention thus also includes a method of preventing graft versus host disease in a mammal. The method comprises contacting a population of hematopoietic cells in the mammal with an antigen presenting cell depleting composition to effect depletion of antigen presenting cells in the population of hematopoietic cells, and transferring donor hematopoietic cells to the mammal, wherein the graft verus host disease is prevented in the mammal by virtue of the depletion of the antigen presenting cells. The population of hematopoietic cells may be contacted with the antigen presenting cell depleting composition in vivo in the mammal. The preferred mammal is a human.

The invention also includes a method of preventing graft versus host disease in a mammal. The method comprises obtaining a population of hematopoietic stem cells from the mammal. A gene is added to the cells which when expressed in the cells is capable of killing the cells. Cells which ahve received the gene are selected by virtue of the fact that the cells are co-transfected with a selectable marker. The mammal is irradiated to remove bone marrow cells in the mammal. The selected cells are added to the mammal and expression of the gene in the selected cells is induced thereby effecting killing of antigen presenting cells in the mammal. The mammal is then provided with an allogenic bone marrow transplant, wherein graft versus host disease is prevented in the mammal by virtue of the killing of the antigen presenting cells.

In a preferred embodiment, the gene is operably linked to an inducible promoter and expression of the gene is effected by administration of an inducer of the promoter to the mammal. In another preferred embodiment, the gene encodes a toxin.

Also included is a method of preventing graft versus host disease in a mammal. This method comprises obtaining a population of hematopoietic stem cells from the mammal, adding to the cells a gene which when expressed in the cells in the presence of a corresponding agent is capable of killing the cells. Cells having the gene are selected. The mammal is irradiated to remove bone marrow cells in the mammal. The selected cells are added to the mammal, and the corresponding agent is also added to the mammal to effect killing of the selected cells in the mammal thereby effecting killing of antigen presenting cells in the mammal. The mammal is provided with an allogenic bone marrow transplant, wherein graft versus host disease is prevented in the mammal by virtue of the killing of the antigen presenting cells.

In a preferred embodiment, the gene is thymidine kinase, the gene is operably linked to a constitutive promoter and the corresponding agent is ganciclovir. In another preferred embodiment, the gene is thymidine kinase, the gene is operably linked to an inducible promoter, the corresponding agent is ganciclovir, and prior to adding the corresponding agent to the mammal, the expression of the gene is induced by administration of an inducer of the promoter to the mammal.

"Prevention of graft versus host disease" in a mammal, as the term is used herein, means reducing the severity of the graft versus host disease which would occur in the absence of any treatment, or ablating graft versus host disease as a result of the treatment.

The type of immunosuppression aimed at APCs which is disclosed herein may be used to prevent GVHD completely or partially in any situation in which allogeneic bone marrow transplantation might be performed. Such situations include, but are not limited to the following: Hematologic malignancies, such as, but not limited to, acute myeloid leukemia, acute lymphoid leukemia, chronic myelogenous leukemia, lymphomas, chronic lymphocytic leukemia, myelodysplasia and preleukemias, multiple myeloma, essential thrombocythemia, myelofibrosis, polycythemia vera, and paroxysmal nocturnal hemaglobinuria. Autoimmune cytopenias, including, but not limited to aplastic anemia, amegakaryocytic thrombocytopenia, immune thrombocytopenia, autoimmune hemolytic anemia, and autoimmune neutropenias. Genetic disorders including, but not limited to hemaglobinopathies such as sickle cell disease and thalasemias, severe combined immune deficiency disorders, such as adenosine deaminase deficiency and lysosomal storage diseases, such as Gaucher's Disease. Other autoimmune diseases including, but not limited to rheumatoid arthritis, systemic lupus erythematosis, Sjogren's syndrome, multiple sclerosis, vasculitides, dermatomyosisitis, polymyositis, and ankylosing spondylitis. Also included is solid organ transplantation. Further, the methods of the invention are useful as immunosuppressive therapy in the absence of allogenic bone marrow transplantation. Because depletion of functional antigen presenting cells is effective in preventing GVHD, one of the most potent in vivo T cell stimuli, it is likely to also be effective outside of the allogeneic bone marrow transplant context as therapy for any of the autoimmune cytopenias or autoimmune diseases disclosed herein.

The invention further encompasses the use pharmaceutical compositions of an appropriate APC depleting composition to practice the methods of the invention, the compositions comprising an appropriate APC depleting composition and a pharmaceutically-acceptable carrier.

As used herein, the term "pharmaceutically-acceptable carrier" means a chemical composition with which an appropriate APC depleting composition may be combined and which, following the combination, can be used to administer the appropriate APC depleting composition to a mammal.

The pharmaceutical compositions useful for practicing the invention may be administered to deliver a dose of between 1 ng/kg/day and 100 mg/kg/day.

Pharmaceutical compositions that are useful in the methods of the invention may be administered systemically in oral solid formulations, ophthalmic, suppository, aerosol, topical or other similar formulations. In addition to the APC depleting composition, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate APC depleting composition according to the methods of the invention.

The invention is now described with reference to the following experimental examples. These examples are provided for the purpose of illustration only and the invention should in no way be construed as being limited to these examples but rather should be construed to encompass any and all variations which become evident as a result of the teaching provided herein.

EXAMPLE 1

Prevention of GVHD by Selective Inactivation of Host APCs

In order to address whether donor or host APCs initiate GVHD, a genetic approach was taken to ask whether host mice whose APCs' were incapable of presenting MHC I restricted peptides would support a GVHD reaction. First, mice were generated that did not express MHC I on their APCs but did express MHC I on target tissues. Such mice were constructed as bone marrow chimeras (FIG. 1) using wild type C57BL/6 (B6; H-$2^b$) hosts and B6 β-2-microglobulin knock out mice ($β_2M^{-/-}$) as bone marrow donors ($β_2M-/-\Rightarrow$B6 chimeras) (Koller et al., 1990, Science 248: 1227–1230). Because $β_2$-microgloblulin is part of the MHC I complex, cells obtained from these mice do not express MHC I and therefore cannot present peptide antigens to CD8$^+$ T cells (Koller et al., 1990, Science 248:1227–1230). After waiting four months to allow for $β_2M^{-/-}$ bone marrow engraftment and APC repopulation, these chimeras were used as recipients in a second allogeneic bone marrow transplant designed to cause GVHD. This was performed essentially as follows. Bone marrow was flushed from femurs and tibias with DMEM plus 10% fetal bovine serum. Red cells were lysed using the NH$_4$Cl/Tris method, washed and resuspended in PBS with 0.5% BSA and 5 mm EDTA. BM cells were T cell depleted with anti-Thy 1.2 labeled microbeads (Miltenyi Biotech, Auburn, Calif.) according to the manufacturer's protocol. T cell depletion was confirmed by staining with a combination of CD4 FITC, CD8 FITC and CD3 PE labeled antibodies (Pharmingen, San Diego, Calif.), clones RM4-5, 53-6.7 and 500-A2, respectively. After exclusion of dead cells by propidium iodide staining, residual T cells were between 0.01–0.06% of total live cells. Thus, T cell depleted C3H.SW (H-$2^b$) bone marrow (C3H.SW T$^-$BM) with or without $10^6$ or $2 \times 10^6$ highly purified C3H.SW CD8$^+$ T cells (FIG. 1) was infused into the previously generated chimeric recipients following a second dose of radiation. As controls, B6 recipients received syngeneic marrow in the first transplant (B6⇒B6), and were then treated identically as the $\beta_2M^{-/-}$⇒B6 chimeras.

Highly purified C3H.SW CD8$^+$ T cells were obtained as follows. CD8+ T cells were isolated by negative depletion of C3H.SW lymph nodes by first staining cells with biotin labeled antibodies against CD4 and CD45R (B220) (clones GK1.5 and RA3-6 B2), and CD11b (clone M1/70) (Pharmingen, San Diego, Calif.), followed by the addition of streptavidin conjugated magnetic beads (Miltenyi Biotech, Auburn Calif.). Negative depletion was performed according to the manufacturer's protocol. To confirm the purity of the CD8+ T cells, cells were stained with antibodies against CD4, CD8, CD11b, and CD45R (B220). Ninety five percent of the cells were CD8+; CD4+ or CD3+/CD8- cells were <0.25%.

Strikingly, in each of three experiments, the $\beta_2M^{-/-}$⇒B6 recipients of BM plus CD8$^+$ T cells were resistant to the induction of acute GVHD (FIG. 2A, left panel). On the other hand, as expected, the B6⇒B6 recipients of C3H.SW BM plus CD8 cells developed severe acute GVHD manifested by hunched posture, erythema of ears and skin, alopecia (FIG. 2A, right panel), weight loss (FIG. 3A), and death. In the first experiment (experiment 1), mice were sacrificed for histologic analysis of liver, back skin, ears, tongue and small bowel and these tissues were examined for pathologic evidence of GVHD. Blinded readings of this pathology are summarized in the Table in FIG. 5. This experiment was performed as follows. Formalin fixed, paraffin embedded sections were stained with hematoxylin and eosin. Slides were coded and were examined blindly by more than one investigator. Small intestine sections were evaluated for overall architectural integrity, degree and type of inflammation in the lamina propria, and epithelial injury. The assessment of epithelial injury consisted of a subjective grading of the number of apoptotic cells within epithelial crypts on a scale of 1–3+ and the degree of mucosal inflammation, both intra-epithelial and lamina propria. For each animal, the degree of activity in each of these areas was then combined to give an overall interpretation of positive, indefinite, or negative for GVHD. Positive animals had an apoptosis score of at least 2+, and had increases in intra-epithelial and lamina propria inflammatory cells that were evident at low to medium power. Indefinite animals had 2+ apoptosis, but no increase in inflammation or other evidence of injury. Negative animals had up to 1+ apoptosis and no other abnormalities. Liver sections were evaluated for the presence and degree (1–3+) of portal inflammatory infiltrates, endothelialitis (portal or central), cholangiolitis, and lobar necroinflammatory changes. An overall interpretation of positive, indefinite or negative for GVHD was given for each animal. Animals received a positive score if mixed inflammatory infiltrates with endothelialitis and/or cholangiolitis were present in any portal tract. Indefinite animals had occasional portal or central lymphocytic infiltrates that lacked other inflammatory cells and lacked cholangiolitis/endothelialitis. Negative animals had essentially no infiltrates, no cholangiolitis and no endothelialitis. Tongue, skin and ear biopsies were graded according tot eh presence of mononuclear cell infiltrates, interface changes, dermal fibrosis, and number of apoptotic cells per linear millimeter. Positive cells had to be at least 1+ in more than one criteria. Negative animals had up to 1+ apoptosis and no other abnormalities. Indeterminate animals were 1+ in only one criteria except apoptosis.

Figure 2B:
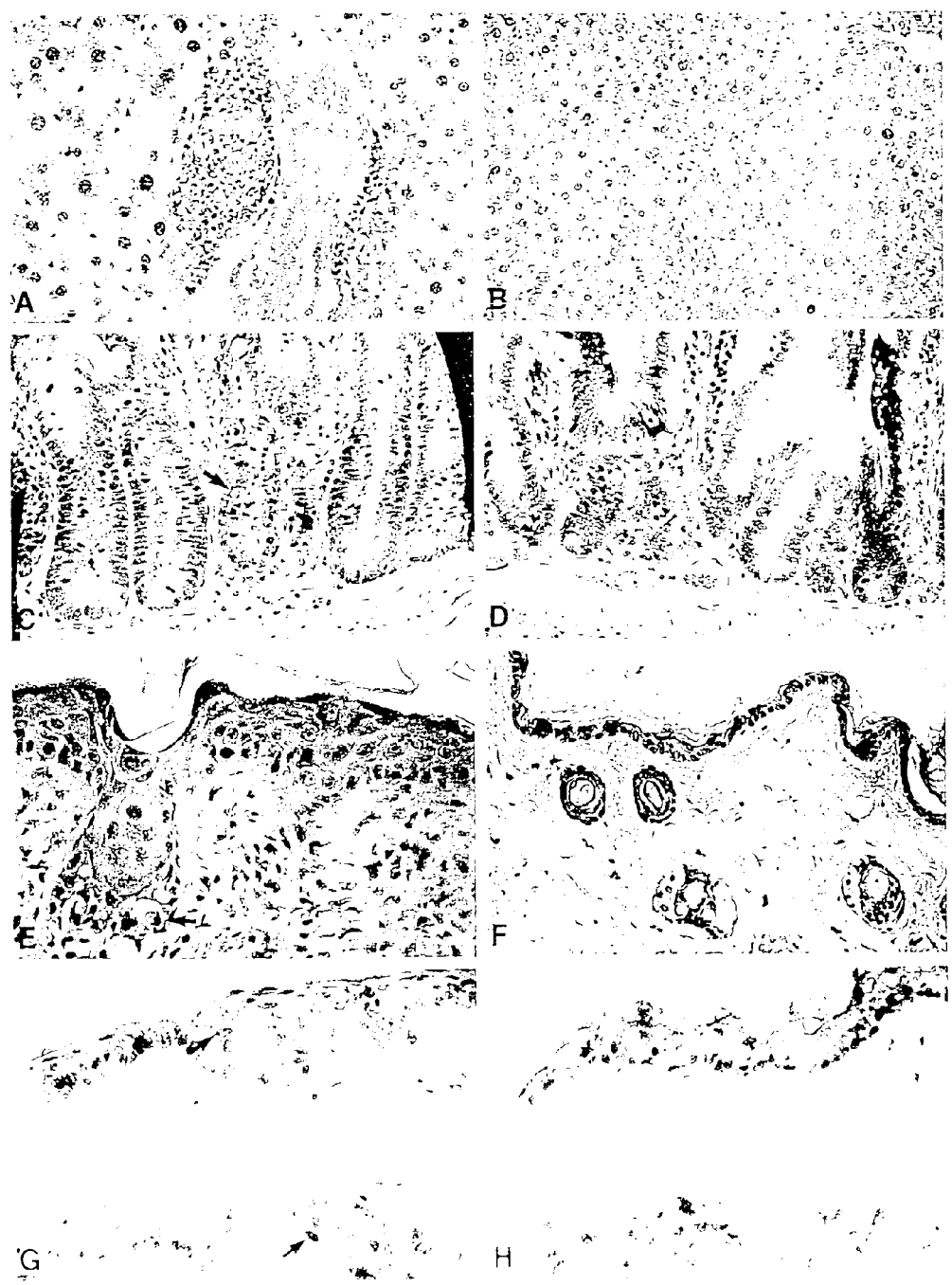
FIG. 2B (comprising Panels A–H) depicts the histology of the mice. Representative $\beta_2 M$-/-⇒B6 (Panels B, D and F) and B6⇒B6 (Panels A, C, E, G and H) recipients of C3H.SW BM and CD8$^+$ T cells are shown. Liver (Panels A and B; small intestine (Panels C and D); skin (Panels E and F). Note periportal mononuclear infiltrates in Panel A; apoptotic cells in small bowel crypts in Panel C (arrow); and mononuclear cell infiltrate, fibrosis, epidermal maturation disarray, and necrotic keratinocytes (arrow) in Panel E. These changes were absent in $\beta_2 M$-/-⇒B6 recipients. Panel G: horseradish peroxidase staining of CD8 positive cells; note CD8 cells invading follicles and epidermis (arrows). Panel H: immunohistochemical staining for CD4 cells from the same mouse as in Panel G. Note the paucity of cells staining for CD4 relative to CD8 in Panel G.
Figure 3A:
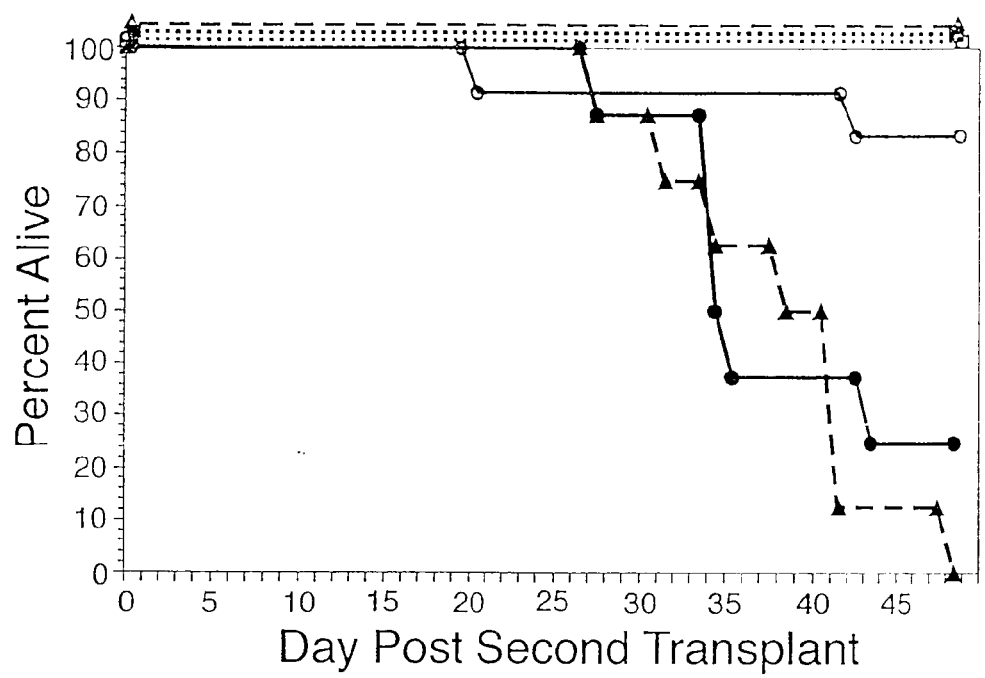
FIG. 3A is a graph depicting the percent weight loss in mice. Mice were individually weighed three times per week, beginning on day 0. Mean weights of mice in Experiment 1 were plotted as percent weight change versus time. The groups are indicated on the figure. When CD8 cells were included as indicated on the Figure, 1×$10^6$ cells were used.
Figure 3B:
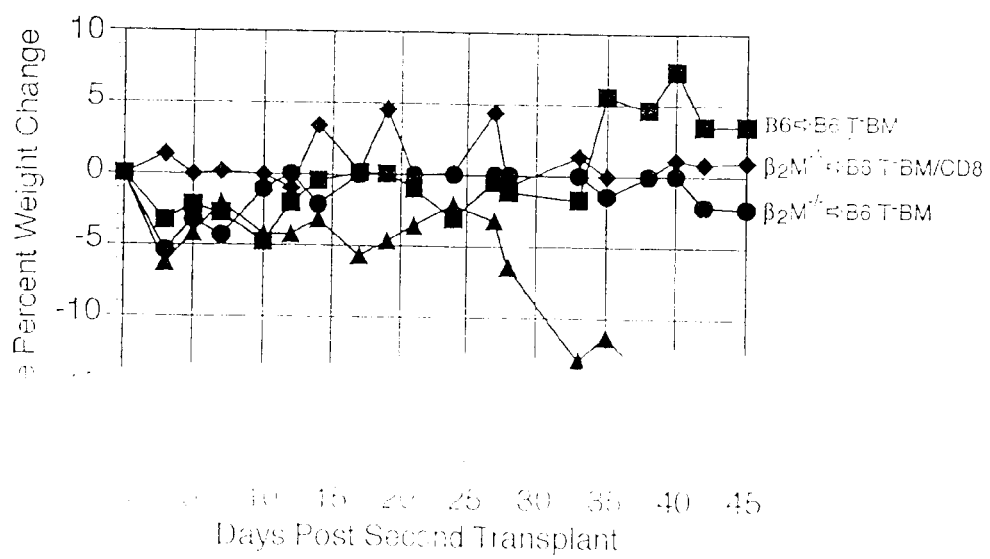
FIG. 3B is a graph depicting the survival of the mice. In a second experiment, recipients of a second transplant were followed for survival. $\beta_2 M^{-/-}$⇒B6 and B6⇒B6 chimeras were irradiated followed by the infusion of C3H.SW T$^-$BM with 0 (--■--B6⇒B6 T⁻BM alone (four mice); --c--β$_2$M-/-⇒B6 T-BM alone (eight mice), 1×10$^6$ (■●■B6⇒B6 T-BM+1×10$^6$ CD8 (eight mice); -⊖-β$_2$M-/-⇒B6 T-BM+1×10$^6$ CD8(twelve mice)), or 2×10$^6$ (■▲■B6⇒B6 T-BM+2×10$^6$ CD8 (eight mice); -Δ-β$_2$M-/-⇒B6 T-BM+2×10$^6$ CD8 (twelve mice)) purified C3H.SW CD8+T cells.

Of 30 tissues examined from $\beta_2M^{-/-}$⇒B6 CD8 recipients, only one ear biopsy was read as having GVHD. In contrast, 26/30 tissues from B6⇒B6 CD8 recipients were read as clearly demonstrating GVHD pathology. Representative histologic sections are shown in FIG. 2B. Immunohistochemical staining of skin obtained from B6⇒B6 CD8 recipients demonstrated CD8$^+$ cells infiltrating the epidermis whereas no CD4$^+$ T cells were seen in this site, confirming the pathogenic role of CD8$^+$ T cells in this model (FIG. 2B; panels G, H).

In a separate experiment (experiment 2) $\beta_2M-/-$⇒B6 and B6⇒B6 chimeras received 0, $1 \times 10^6$ or $2 \times 10^6$ C3H.SW CD8 cells and C3H.SW T$^-$BM, and were followed for survival rather than being sacrificed for pathologic analysis (FIG. 4). Again, GVHD was markedly inhibited or absent in mice with $\beta_2M^{-/-}$ BM. Six of eight and 8/8 B6⇒B6 recipients of $1 \times 10^6$ and $2 \times 10^6$ C3H.SW CD8 cells died with clinical GVHD, whereas only two deaths occurred in the 24 $\beta_2M^{-/-}$⇒B6 chimeric recipients of C3H.SW CD8 cells (p=0.0024, Fisher's exact test; comparison between all B6⇒B6 and $\beta_2M^{-/-}$⇒B6 CD8$^+$ T cell recipients). It is unlikely that the $\beta_2M^{-/-}$⇒B6 BM/$1 \times 10^6$ death 10 days post the second transplant was due to GVHD as it occurred 15 days prior to the earliest onset of GVHD lethality seen in this system. No clinical GVHD developed in any of the $\beta_2M^{-/-}$⇒B6 $2 \times 10^6$ CD8 recipients.

In a third similar experiment in which all mice received $2 \times 10^6$ CD8 T cells, GVHD was again inhibited in the $\beta_2M^{-/-}$⇒B6 CD8 cell recipients. However, in this case, some clinical GVHD was observed among 3 of 8 mice in this group (compared to 7 of 8 positive controls), although this GVHD was delayed (40% longer mean time to onset) and was less severe (46% less average weight loss) than was observed in the B6⇒B6 CD8 cell recipients.

The finding of milder and delayed "breakthrough" GVHD among 3 of 38 $\beta_2M^{-/-}$⇒B6 CD8 cell recipients over three experiments suggested that replacement of host MHC I$^+$ APCs with $\beta_2M^{-/-}$ MHC I$^-$ APCs might be somewhat variable and incomplete. Ideally, in the $\beta_2M^{-/-}$⇒B6 chimeras, 100% of BM-derived APC, including DC, macrophages, and B cells, would be MHC I negative. To determine the degree to which this was actually achieved, flow cytometry analysis was performed on spleen and lymph node cells from a cohort of $\beta_2M^{-/-}$⇒B6 chimeras within one week of the second allogeneic transplant (Experiment 2; FIG. 4). Dendritic cells were identified using four color flow cytometry. Although most of the APC's were indeed MHC I negative, in every case there were residual MHC I$^+$ cells. 11/12 mice had less than 3% residual MHC I$^+$ splenic dendritic cells; 1 chimera had 17.8% MHC I$^+$ splenic dendritic cells. In lymph nodes, a greater percentage of residual MHC I$^+$ dendritic cells (median 7.9%; range: 5–15%) was observed. For macrophages, as with dendritic cells, replacement of MHC I$^+$ cells was more complete in spleens than in lymph nodes. Medians of 4.7% (range 2.9–6.4%) and 23.4% (range 15.2–28.9%) of splenic and lymph node macrophages were MHC I+. Surprisingly, the extent of residual host-derived macrophages was greater than for dendritic cells. There were few residual host-derived splenic (median 1.6%; range 0.8–2.1%) and lymph node (median 2.7%; range 1.4–4.8%) B cells. These data indicate that complete depletion of MHC I+ APCs is not required for substantial clinical protection from GVHD, and in addition support the hypothesis that the few cases of breakthrough GVHD were likely due to variable APC replacement. From these data, the important APC cell type (s) cannot be inferred, although DC seem a reasonable candidate (Bancereau et al., 1998, Nature 392:245–252).

The failure of the $\beta_2M^{-/-} \Rightarrow B6$ CD8 recipients to develop GVHD was not due to rejection of donor CD8 cells or to the failure of donor C3H.SW marrow to engraft. C3H.SW and B6 mice express different alleles of the CD5 pan T cell surface antigen (C3H.SW express CD5.1; B6 express CD5.2). Using a monoclonal antibody against the CD5.1 allele, donor CD8 C3H.SW T cells were observed in the $\beta_2M^{-/-} \Rightarrow B6$ chimeras. Similarly, nearly all of the CD11b and CD 11c expressing cells in the $\beta_2M^{-/-} \Rightarrow B6$ chimeras that underwent the second transplant were MHC I+, demonstrating donor C3H.SW APC engraftment.

These experiments establish that in an MHC matched, multiple minor histocompatibility antigen mismatched alloBMT model analogous to most human alloBMTs, functional host APCs are absolutely required to initiate CD8+ T cell dependent GVHD. Also of note, "semi-professional" antigen presentation by nonhematopoietic cells was also inadequate to induce GVHD. Although there is clear evidence of cross priming in a variety of experimental situations (Matzinger et al., 1977, Cell. Immunol. 33:92–100; Bevan, 1976, J. Exp. Med. 143:1283–1288; Bevan, 1995, J. Exp. Med. 182:639–641; Carbone et al., 1989, Cold Spring Harbor Symp. Quant. Biol. 1:551–555; Huang et al., 1994, Science 264:961–965; Huang et al., 1996, Immunity 4:349–355; Srivastava et al., 1994, Immunogenetics 39:93–98; Arnold et al., 1995, J. Exp. Med. 182:885–889; Kurts et al., 1998, J. Exp. Med. 188:409–414; Carbone et al., 1990, J. Exp. Med. 171:377–387), in the $\beta_2M^{-/-} \Rightarrow B6$ chimeras described here, cross priming of donor derived APCs with host peptides was insufficient to generate a GVHD reaction. Radiation and chemotherapy lead to large scale cell death and release of intracellular contents, including heat shock protein/peptide complexes which have been hypothesized to mediate cross priming (Udono et al., 1993, J. Exp. Med. 178:1391–1396; Lammert et al., 1997, Eur. J. Immunol. 27:923–927; Arnold et al., 1997, J. Exp. Med. 186:461–466). Although these materials would be equally available to donor or host APCs, released host antigens presented on donor APC did not stimulate GVHD.

The results presented herein could have a substantial impact on how acute GVHD is both prevented and treated. Specific targeting of host APCs prior to the conditioning regimen will prevent GVHD from occurring at all, eliminating the need for prolonged immunosuppression. The analysis of a cohort of $\beta_2M^{-/-} \Rightarrow B6$ chimeras prior to the second GVHD inducing transplant suggests that 100% ablation of host APCs will not be necessary in order to decrease donor T cell activation and the resultant GVHD. The model of CD8-dependent, miHA specific GVHD closely mirrors the human situation, and will be useful in preclinical studies of this strategy. If successful, such an approach could both expand the range of diseases routinely treated with alloBMT to include prevalent inherited disorders such as sickle cell anemia and the thalassemias, and allow more routine use of matched unrelated and antigen mismatched hematopoietic progenitor allografts. Also, as the peripheral T cell compartment in adult hosts post alloBMT is derived from the donor graft (Mackall et al., 1997, Blood 89:3700–3707; Mackall et al., 1997, Immunol. Today 18:245–251; Mackall et al., 1993, Blood 82:2585–2594), the ability to deliver larger T cell doses without GVHD should result in more complete immune reconstitution.

These data also provide new hypotheses to explain several intriguing clinical observations in clinical allogeneic bone marrow transplantation. It has long been recognized that a subset of alloBMT recipients have self-limited GVHD (Chao et al., 1996, In: Graft-Vs-Host Disease, Ferrara et al., eds., Marcel Dekker Inc., NY). Although the remission of GVHD has been presumed to reflect a state of acquired T cell tolerance, the present data suggest that replacement of host APCs, both by passive turnover and direct elimination of host APCs by a Graft-versus-APC reaction, may be another mechanism by which GVHD is down-regulated. More recently, infusions of T cells from the original BM donors have been given to relapsed leukemia patients months to years following the initial alloBMT. Considering the high doses of T cells given, these patients have demonstrated dramatically reduced GVHD relative to what has been observed when T cells are given at the time of transplantation (Sullivan et al., 1989, New Engl. J. Med. 320:828–834; Sullivan et al., 1986, Blood 67:1172–1175; Kolb et al., 1995, Blood 86:2041–2050; Collins et al., 1994, Blood 84:333a). Other investigators have speculated that the tissue damage and high cytokine levels induced by the conditioning regimen provides a milieu that enhances the development of GVHD (Ferrara et al., 1994, Bone Marrow transplantation 14:183–184; Ferrara et al., 1993, transplantation Proceedings 25:1216–1217; Ferrara, 1993, Curr. Opinion in Immunol. 5:794–799), which would not be the case during the T cell infusion. While a lack of tissue damage and cytokine release may in part explain reduced GVHD, it is hypothesized that the host APCs that drive GVHD reactions would be replaced by donor APCs months to years after the initial BMT, thus reducing the chance that a donor CD8+ T cell would interact with a GVHD inducing host APC.

The experiments presented herein provide the impetus for a different strategy for reducing GVHD, namely, host APC depletion. This strategy is therefore free of the problems associated with T cell depletion of marrow allografts, such as failure of engraftment, poor immune reconstitution, and lack of immunoreactivity against the tumor. If these potential benefits could be realized clinically, the scope and efficacy of alloBMT could be dramatically expanded, resulting in more effective treatment of many leukemias and neoplasms as well as cure of genetic stem-cell based defects such as sickle cell anemia and thalassemia.

EXAMPLE 2

Evidence for Depletion of Cells in Normal Host Animals

Having demonstrated that mice having genetically impaired antigen presenting cells were resistant to the induction of acute GVHD, experiments to demonstrate proof of principle that this could be accomplished in a non-genetic fashion in normal host animals were conducted. Such an approach models the clinical situation in humans. Thus, the feasibility of antibody mediated dendritic cell depletion was assessed in the experiments described herein. This approach has been used to deplete lymphocyte subsets in mice and has been approved for treatment of human malignancies (Baselga et al., 1998, Cancer Res. 58(13):2825–2831; Bolognesi et al., 1998, Brit. J. Haematol. 101(1):179–188; Collinson et al., 1994, Internatl. J. Immunopharmacol. 16(1):37–49; Conry et al., 1995, J. Immunotherapy with emphasis on Tumor Immunology 18(4):231–241; Francisco et al., 1998, Leukemia and Lymphoma 30(3–4):237–245; Ghetie et al., 1997, Mol. Med. 3(7):420–427; Reitman et al., 1998, Adv. Drug Deliv. Rev. 31(1–2):53–88; Maurer-Gebhard et al., 1998, Cancer Res. 58(12):2661–2666).

The integrin, CD11c, was selected as a target antigen. CD11c is used to identify murine dendritic cells (Maraskovsky et al., 1996, J. Exp. Med. 184(5):1953–1962). It has been shown to be expressed on all subsets of dendritic cells. Hamster anti-CD11c hybridoma 33D1 was purchased from the American Tissue Culture Cell repository (Metlay et al., 1990, J. Exp. Med. 171(5):1753–1771). Antibody was generated by both tissue culture growth and ascites production. C57BL6/J mice received intraperitoneal (i.p.) injections with 500 μg of 33D1 or an equal volume of phosphate buffered saline (PBS) on two consecutive days. Mice were sacrificed 3–5 days after injection to assess the impact of 33D1 administration.

Dendritic cell enriched cell preparations obtained from spleens and lymph nodes were assessed for whether the in vivo delivered 33D1 was bound to dendritic cells. The results for the spleen cells are displayed in FIG. 6; similar results were obtained in the case of lymph node cells. Dendritic cells were identified using 4 color flow cytometry by their failure to stain with antibodies directed against myeloid (Gr-1), erythroid (TERR 119), T cell (CD3) or B cell (CD45R; B220) markers and their expression of CD11b, CD11c, and MHC II. Dendritic cells display a classic immunophenotype of $CD11c^+/MHC\ II^+$ with or without expression of CD11b. When flow cytometry was performed, a second biotin conjugated anti-CD11c antibody, clone HL3, purchased from Pharmingen (San Diego, Calif.) was used. Prior staining with 33D1 prevents binding of HL3 to the cells.

Dendritic cells obtained from PBS treated mice were readily detected using HL3 (FIG. 6, Panel A). Preincubation of the cells with 33D1 prevented detection with HL3 (FIG. 6, Panel B). The use of biotin labeled monoclonal antibodies directed against hamster IgG restored the ability to identify CD11 c expressing cells (FIG. 6, Panel F). In spleen and lymph node cells obtained from in vivo 33D1 treated mice, staining with HL3 was reduced nearly 100 fold (FIG. 6, Panel E), an effect equivalent to ex-vivo blockade as shown in FIG. 6, Panel C. Staining using an anti-hamster reagent again facilitated the identification these cells (FIG. 6, Panel F). Thus, in vivo treatment with 33D1 is capable of binding a high percentage of CD11c molecules in 100% of dendritic cells.

Although 33D1 binding did not eliminate these cells, this experiment provides proof of principle for the use of toxin conjugated or radiolabeled antibodies directed against CD11c or other antigens.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of preventing graft versus host disease in a host mammal, said method comprising contacting a population of hematopoietic cells in said host mammal with an antigen presenting cell depleting composition to effect depletion of antigen presenting cells in said population of hematopoietic cells, and transferring donor hematopoietic cells to said host mammal, wherein said graft versus host disease is prevented in said host mammal by virtue of said depletion of said antigen presenting cells, wherein said antigen presenting cells are selected from the group consisting of dendritic cells and macrophages, and further wherein said antigen presenting cell depleting composition comprises an immunotoxin.

2. The method of claim 1, wherein said host mammal is a human.

3. The method of claim 1, wherein said donor hematopoietic cells are human hematopoietic cells.

4. The method of claim 1, wherein the toxin component of said immunotoxin is selected from the group consisting of ricin, diptheria toxin and pseudomonas exotoxin A.

5. The method of claim 1, wherein said antigen presenting cell depleting composition is a chimeric composition comprising an antibody and a toxin.

6. The method of claim 5, wherein said toxin is selected from the group consisting of ricin, diptheria toxin and pseudomonas exotoxin A.

7. The method of claim 5, wherein said antibody is selected from the group consisting of antibody specific for CD1a, antibody specific for CD11c, antibody specific for MHCII, antibody specific for CD11b, antibody specific for DEC205, antibody specific for B71, antibody specific for B72, antibody specific for CD40, antibody specific for Type I lectins and antibody specific for Type II lectins.

8. The method of claim 1, wherein said depletion of said antigen presenting cells comprises impairing their antigen presenting cell function.

9. The method of claim 1, wherein said depletion of the antigen presenting cells comprises killing said antigen presenting cells.

* * * * *